United States Patent
Castillo et al.

(10) Patent No.: US 11,295,854 B1
(45) Date of Patent: Apr. 5, 2022

(54) PROXIMITY-BASED PATIENT CHECK-IN COMPUTING SYSTEM

(71) Applicant: Allscripts Software, LLC, Raleigh, NC (US)

(72) Inventors: Jennifer Castillo, Harwood Heights, IL (US); Ankit Singh, Apex, NC (US); Mark Plunkett, Libertyville, IL (US); Devin Brown, Durham, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 168 days.

(21) Appl. No.: 16/127,298

(22) Filed: Sep. 11, 2018

(51) Int. Cl.
*G16H 40/20* (2018.01)
*G16H 10/60* (2018.01)

(52) U.S. Cl.
CPC ............. *G16H 40/20* (2018.01); *G16H 10/60* (2018.01)

(58) Field of Classification Search
CPC ........ G16H 10/60; G16H 40/20; G16H 50/70; G16H 50/20
USPC .......................................................... 705/3
See application file for complete search history.

(56) References Cited

U.S. PATENT DOCUMENTS

| 6,347,329 | B1 * | 2/2002 | Evans ................... G06F 19/325 709/202 |
| 6,830,180 | B2 | 12/2004 | Walsh |
| 2005/0187948 | A1 | 8/2005 | Monitzer et al. |
| 2007/0226010 | A1 | 9/2007 | Larsen |
| 2007/0282654 | A1 | 12/2007 | Sarkar |
| 2010/0017222 | A1 | 1/2010 | Yeluri et al. |
| 2011/0153341 | A1 | 6/2011 | Diaz |
| 2011/0224998 | A1 * | 9/2011 | Schoenberg ......... G06Q 10/109 705/1.1 |
| 2012/0053963 | A1 | 3/2012 | Seymour et al. |
| 2012/0209622 | A1 * | 8/2012 | Larsen ................ G06Q 10/109 705/2 |

(Continued)

FOREIGN PATENT DOCUMENTS

| EP | 2843567 A1 * | 3/2015 | ........... G06F 16/284 |
| WO | WO-2015191562 A1 * | 12/2015 | ............. G06Q 10/10 |

OTHER PUBLICATIONS

Ana-Monica Racila, Providers and Patients as Activists: Bureaucratic Encorpment in Two Midwest GenderAffirming Health Clinics, 2020, ProQuest (Year: 2020).*

*Primary Examiner* — Hiep V Nguyen
(74) *Attorney, Agent, or Firm* — Calfee, Halter & Griswold LLP

(57) ABSTRACT

An improved patient check-in system for healthcare appointments is disclosed herein. Prior to a datetime of a healthcare appointment of a patient, an electronic health records application (EHR) receives a first message originating from a patient computing device of the patient. The first message includes a location of the patient and patient information for the patient. Responsive to receiving the first message, the EHR stores the patient information in a cache. The EHR also places a placeholder for the patient in a queue that indicates an order in which healthcare appointments for patients at the healthcare facility are to occur. Subsequently, the EHR receives a second message generated by the patient computing device indicating that the patient has arrived at the healthcare facility for the healthcare appointment. The EHR transfers the patient information from the cache to a data store accessible to the EHR.

20 Claims, 7 Drawing Sheets

(56) References Cited

U.S. PATENT DOCUMENTS

2016/0253464 A1* 9/2016 Balwani ............... G06Q 50/22
705/2

* cited by examiner

402

| PATIENT ID | INSURER |
|---|---|
| 1 | INSURER 1 |
| 2 | INSURER 2 |
| 3 | INSURER 3 |
| 4 | INSURER 3 |
| 5 | INSURER 4 |

404

| PATIENT ID | ALLERGIES |
|---|---|
| 1 | ALLERGIES 1, 2, AND 3 |
| 2 | NONE |
| 3 | ALLERGY 4 |
| 4 | ALLERGY 2 |
| 5 | ALLERGIES 4 AND 5 |

406

| PATIENT ID | MEDICATIONS |
|---|---|
| 1 | MEDICATIONS 1 AND 2 |
| 2 | MEDICATIONS 3 AND 4 |
| 3 | MEDICATION 1 |
| 4 | MEDICATIONS 5 AND 6 |
| 5 | MEDICATIONS 6 AND 7 |

408

| PATIENT ID | ZIP CODE | AGE | ADDRESS | SEX |
|---|---|---|---|---|
| 1 | ZIP CODE 1 | AGE 1 | ADDRESS 1 | M |
| 2 | ZIP CODE 2 | AGE 2 | ADDRESS 2 | M |
| 3 | ZIP CODE 3 | AGE 3 | ADDRESS 3 | F |
| 4 | ZIP CODE 4 | AGE 4 | ADDRESS 4 | M |
| 5 | ZIP CODE 5 | AGE 5 | ADDRESS 5 | F |

FIG. 4

PROXIMITY-BASED PATIENT CHECK-IN COMPUTING SYSTEM

BACKGROUND

Electronic health records applications (EHRs) are computer-executable applications that are configured to assist healthcare workers with providing care to patients. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve data from a patient record maintained by an EHR to relatively quickly ascertain problems being experienced by the patient, medications currently being taken by the patient, and so forth.

Some EHRs are configured with patient check-in functionality which enables a patient to be checked-in for a healthcare appointment at a healthcare facility. Conventionally, when the patient arrives at the healthcare facility for the healthcare appointment, he or she will relay his or her patient information that is to be used during the healthcare appointment to a healthcare worker. For instance, the patient information may include a name of the patient, an address of the patient, a sex of the patient, a list of any allergies the patient may have, a list of active (i.e., current) medications that the patient is taking, and/or insurance information of the patient. The EHR will then receive the patient information as input from the healthcare worker and the EHR will store the patient information in a data store along with an indication that the patient has checked-in for the healthcare appointment. Another healthcare worker (e.g., a physician) may then conduct the healthcare appointment with the patient. In an example, after the healthcare appointment is conducted, the EHR may use the patient information to generate an electronic prescription.

Conventional patient check-in systems provided by EHRs have various deficiencies. First, patients often are late to scheduled healthcare appointments and/or reschedule healthcare appointments. This necessitates updating patient data maintained by the EHR. However, data maintained by EHRs is often stored in highly normalized forms. As such, updating the patient data involves updating many different tables storing the patient information, which is undesirable, especially when a healthcare appointment is changed multiple times. Second, conventional patient check-in systems are not configured to automatically reschedule appointments based upon patient distance to a healthcare facility. Third, conventional patient check-in systems do not provide the patient with the ability to visually check the status of other appointments on a computing device operated by the patient.

SUMMARY

The following is a brief summary of subject matter that is described in greater detail herein. This summary is not intended to be limiting as to the scope of the claims.

Disclosed herein are various technologies pertaining to patient check-in functionality of an electronic health records application (EHR). The EHR is a distributed application that includes both server-side functionality (server EHR) and client-side functionality (client EHR). The EHR facilitates more efficient check-in of patients for healthcare appointments at a healthcare facility. The EHR also facilitates dynamically rescheduling of appointments based in part upon patient proximity to the healthcare facility.

In operation, the server EHR schedules a healthcare appointment for a patient at a healthcare facility for a datetime (e.g., a date and a time on the date). In an embodiment, a medication is to be prescribed to the patient during the healthcare appointment. Prior to the datetime of the healthcare appointment, it is contemplated that the patient begins transit to the healthcare facility. As such, a patient computing device operated by the patient may generate and cause a first message to be received by the server EHR. The first message indicates that the patient has begun transit to the healthcare facility. The first message comprises a location of the patient (as ascertained by a geolocation component of the patient computing device) as well as patient information for the patient. The patient information for the patient may include an identifier for the patient (e.g., a name of the patient, a medical record number (MRN), etc.), an age of the patient, an address of the patient, insurance information of the patient, a list of allergies of the patient, and/or a list of (active) medications of the patient.

In a first embodiment, the patient computing device receives the patient information as manual input from the patient. In the first embodiment, the patient computing device may store the patient information in a data store of the patient computing device for future use.

In a second embodiment, the first message initially fails to include at least some of the patient information. For instance, the first message may include an identifier for the patient, but may fail to include the list of allergies of the patient, the list of active medications of the patient, etc. The patient computing device (by way of a client patient portal application) transmits the first message (including the identifier for the patient) to a server patient portal application. The patient portal application retrieves the patient information for the patient based upon the identifier for the patient and causes the patient information to be included in the first message. The server patient portal application then routes the first message to the server EHR.

Responsive to receiving the first message, the server EHR stores the patient information for the patient in a cache accessible to the server EHR. In an embodiment, the patient information may be stored in denormalized form.

The server EHR also places a placeholder for the patient in a computer-implemented queue for healthcare appointments at the healthcare facility. The queue comprises placeholders for healthcare appointments at the healthcare facility. An ordering of the placeholders in the queue is indicative of an order in which the healthcare appointments are to occur at the healthcare facility. A position of the placeholder in the queue is based upon the datetime for the healthcare appointment and a distance between the location of the patient and a location of the healthcare facility.

As the patient travels to the healthcare facility, the patient computing device may cause the server EHR to receive a current location of the patient computing device (and hence the patient) at certain time intervals. In an example, the server EHR may determine that based upon the datetime for the appointment and the current location of the patient, the patient will fail to arrive on time for the healthcare appointment. The server EHR may be configured to reschedule the healthcare appointment for the patient responsive to the determination. In another example, the server EHR may determine that a second patient having a second healthcare appointment at a second datetime that is to occur immediately prior to the healthcare appointment will fail to arrive at the second datetime. In the event the server EHR determines that that the patient will arrive at the healthcare facility prior to or at the second datetime, the server EHR may be configured to reschedule the healthcare appointment and the second healthcare appointment such that the healthcare appointment occurs at the second datetime instead of the datetime.

When the patient arrives (or is about to arrive) at the healthcare facility, the patient computing device may generate a second message and cause the second message to be received by the server EHR. The second message indicates that the patient has arrived (or is about to arrive) at the healthcare facility.

Responsive to receiving the second message, the server EHR may transfer the patient information for the patient from the cache to a data store accessible to the server EHR such that the patient information is stored in the data store. In an embodiment, the patient information in the data store may be stored in a highly normalized form. The server EHR may also remove the placeholder for the patient from the queue. The healthcare worker may then conduct the healthcare appointment with the patient. In an embodiment, an electronic prescription may be generated from the patient information now retained in the data store. Subsequently, the server EHR may purge the patient information from the cache.

The above-described technologies present various advantages over conventional patient check-in systems. First, through use of a cache that temporarily stores patient information of a patient, the above-described technologies reduce the number of times the data store of the server EHR is accessed, thus saving computing resources, especially when a healthcare appointment is rescheduled multiple times. Second, above-described technologies enable automatic rescheduling of healthcare appointments based in part upon patient proximity to a healthcare facility. Third, the above-described technologies provide a patient with the ability to visually check the status of other appointments on a computing device.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 4 is a depiction of tables for patients that can be stored in a cache.

DETAILED DESCRIPTION

Figure 1:
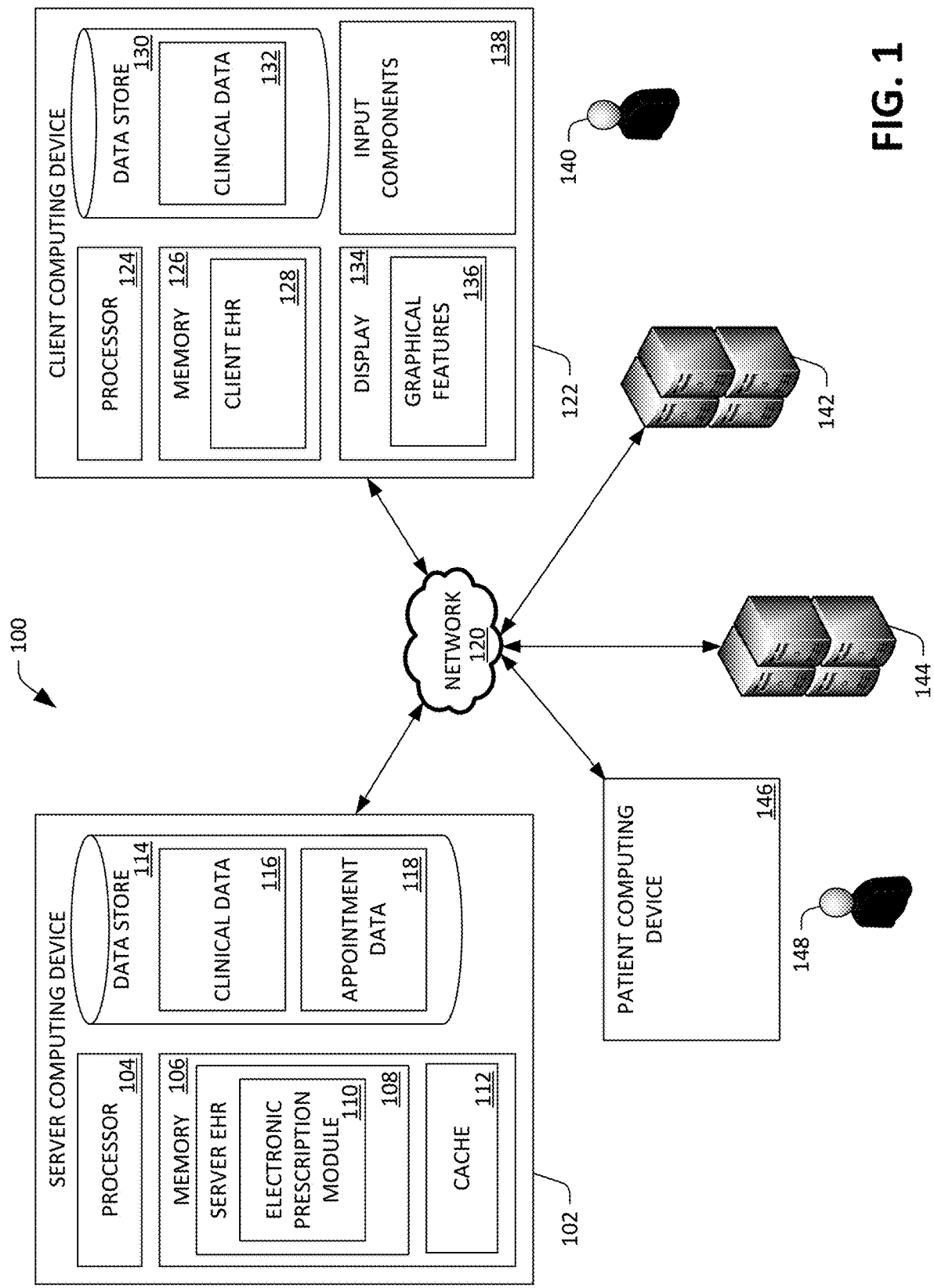
FIG. 1 is a functional block diagram of an exemplary computing system that facilitates patient check-in for healthcare appointments.

Various technologies pertaining to patient check-in for a healthcare appointment are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing system 100 that facilitates patient check-in for healthcare appointments is illustrated. The computing system 100 includes a server computing device 102. The server computing device 102 comprises a processor 104 and memory 106, wherein the memory 106 has a server electronic health records application (server EHR) 108 loaded therein. In general, the server EHR 108 (when executed by the processor 104) is configured to perform a variety of tasks related to patient healthcare in a healthcare facility (e.g., patient intake, prescription generation, patient record creation and maintenance, etc.).

The server EHR 108 may include an electronic prescription module 110. The electronic prescription module 110 is configured to generate electronic prescriptions for patients. The electronic prescription module 110 may also be configured to cause the electronic prescription to be transmitted to an electronic device (e.g., a computing device) of a pharmacy that is to fill the electronic prescription.

The memory 106 may also include a cache 112. As will be described in greater detail below, the cache 112 is configured to temporarily store patient information for patients. In an embodiment, the cache 112 may store patient information for patients in a highly denormalized form. Although the cache 112 is depicted as being stored in the memory 106, other possibilities are contemplated. For instance, in an embodiment, the cache 112 may be stored in other memory (i.e., high-performance memory) or one or more solid state drives (SSDs).

The server computing device 102 may additionally comprise a data store 114. The data store 114 may comprise clinical data 116 for patients, as well as appointment data 118 for patients. The clinical data 116 can include electronic health records, prescription records, claims data, patient/disease registries data, health surveys data, and/or clinical trials data. The appointment data 118 includes datetimes for healthcare appointments of patients that are to occur at a healthcare facility. The appointment data 118 may also include identifiers for patients, identifiers for healthcare workers that are to conduct the healthcare appointments, etc. The clinical data 116 may be stored in a normalized form. For instance, some or all of the clinical data 116 may be stored in third normal form (3NF), elementary key normal form (EKNF), Boyce-Codd normal form (BCNF), fourth normal form (4NF), essential tuple normal form (ETNF), fifth normal form (5NF), domain-key normal form (DKNF), or sixth normal form (6NF). Although the clinical data 116 and the appointment data 118 are depicted as being retained in the data store 114, it is to be understood that the clinical data 116 and the appointment data 118 may be retained in separate data stores. In an embodiment, the appointment data 118 may be stored as part of the clinical data 116. Furthermore, it is to be understood that certain portions of the clinical data 116 may be retained in separate data stores.

The computing system 100 may include a client computing device 122 operated by a healthcare worker 140. In an example, the client computing device 122 may be a tablet computing device. The client computing device 122 may be in communication with the server computing device 102 by way of a network 120 (e.g., the Internet, intranet, etc.). The client computing device 122 comprises a processor 124 and memory 126, wherein the memory 126 has a client electronic health records application (client EHR) 128 loaded therein. In general, the client EHR 128 (when executed by the processor 124) is configured to interface with the server EHR 108 executing on the server computing device 102, thereby providing the healthcare worker 140 with access to functionality of the server EHR 108.

The client computing device 122 may include a data store 130 comprising clinical data 132 about patients. It is understood that there may be overlap between the clinical data 132 stored in the data store 130 and the clinical data 116 stored in the data store 114.

The client computing device 122 may include a display 134, whereupon graphical features 136 may be presented thereon. For instance, a graphical user interface (GUI) may be presented as part of the graphical features 136. The client computing device 122 may additionally include input components 138 suitable for data input. For instance, the input components 138 may include a mouse, a keyboard, a touchscreen, a trackpad, a scroll wheel, a microphone, a camera, a video camera, etc.

In an embodiment, the computing system 100 may include a second server computing device 142. The second server computing device 142 comprises a processor (not shown) and memory (not shown), wherein the memory includes an electronic health records agent application (EHR agent) loaded therein. In general, the EHR agent (when executed by the processor) is configured to retrieve and maintain clinical information for patients from sources inaccessible to the server EHR 108. For instance, the EHR agent may retrieve and maintain clinical information for patients from other EHRs, health information exchanges (HIEs), third-party applications, etc. The EHR agent may maintain such information in a data store (not shown) accessible to the EHR agent.

The computing system 100 may include a third server computing device 144. The third server computing device 144 comprises a processor (not shown) and memory (not shown), wherein the memory has a server patient portal application loaded therein. In general, the server patient portal application (when executed by the processor) is configured to allow a patient to access his or her health data, including prescriptions medications, health records, communications with healthcare providers, insurance information, input self-reported patient health data, schedule healthcare appointments, etc. As such, the server patient portal application may maintain a subset of the clinical data for patients in a data store (not shown) accessible to the server patient portal application. Thus, the server EHR 108 may be configured to provide the server patient portal application with the clinical data, wherein an administrator (not shown) of the server EHR 108 can set forth polices as to what data is included in the clinical data of the server patient portal application. In addition, the server patient portal application can maintain data provided directly by patients to the server patient portal application.

The computing system 100 additionally includes a patient computing device 146 of a patient 148. The patient computing device 146 may be a mobile computing device, such as a tablet computing device, a smartphone, or a wearable computing device (e.g., a smartwatch). In an embodiment, the patient computing device 146 may be integrated into a vehicle of the patient 148. The patient computing device 146 is in communication with the server computing device 102 and/or the third server computing device 144 by way of the network 120 (or another network).

Figure 2:
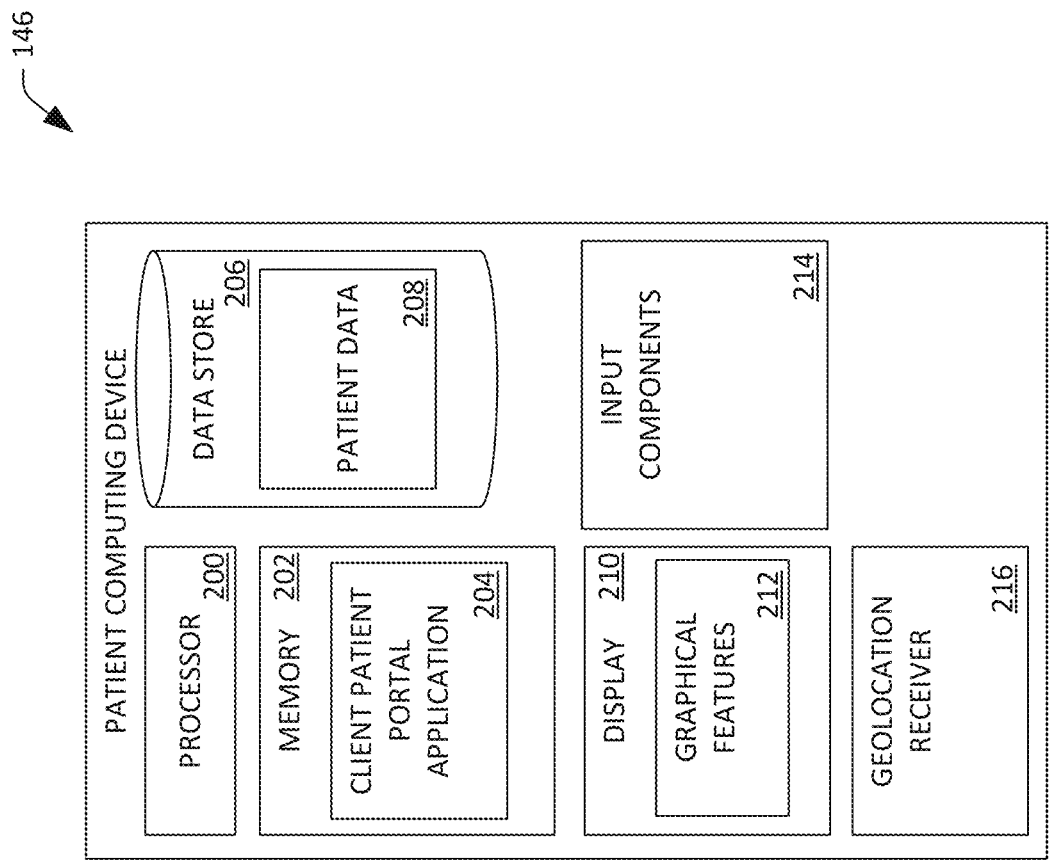
FIG. 2 is a functional block diagram of an exemplary patient computing device.

Referring now to FIG. 2, the patient computing device 146 comprises a processor 200 and memory 202. The memory 202 may include a client patient portal application 204. In general, the client patient portal application 204 (when executed by the processor 200) is configured to communicate with the server patient portal application in order to interface with the server patient portal application to allow the patient 148 to access his or her health data maintained by the server patient portal application.

The patient computing device 146 may include a data store 206 that retains patient data 208 for the patient 148. The patient data 208 may be a subset of the clinical data for the patient. For example, the patient data 208 may include the patient information for the patient 148 discussed above (e.g., the identifier for the patient 148, the list of allergies of the patient 148, etc.).

The patient computing device 146 may include a display 210, whereupon graphical features 212 may be presented thereon. For instance, a graphical user interface (GUI) may be presented as part of the graphical features 212. The patient computing device 146 may additionally include input components 214 suitable for data input. For instance, the input components may include a mouse, a keyboard, a touchscreen, a trackpad, a scroll wheel, a microphone, a camera, a video camera, etc.

The patient computing device 146 may include a geolocation receiver 216 that is configured to ascertain a current location of the patient computing device 146 (that is reflective of a current location of the patient 148). For example, the geolocation receiver 216 may be a global positioning system (GPS) receiver that is configured to ascertain a current location (GPS coordinates) of the patient computing device 146 via communication with space-based radionavigation satellites.

With reference generally now to FIGS. 1 and 2, operation of the computing system 100 is now set forth. It is contemplated that the patient 148 requires a healthcare appointment at a healthcare facility. As such, the server EHR 108 schedules a healthcare appointment for the patient 148 at the healthcare facility for a datetime (i.e., a date and a time). In an example, a medication is to be prescribed to the patient 148 during the healthcare appointment.

Prior to the datetime, the patient 148 may begin transit to the healthcare facility for the healthcare appointment and the patient computing device 146 causes a first message to be received by the server EHR 108. For instance, the patient computing device 146 may receive input from the patient 148 causing the patient computing device 146 to generate and transmit the first message. In an embodiment, the patient computing device 146 may be configured to determine that the patient 148 has begun transit and may be configured to automatically generate and transmit the first message.

The first message indicates that the patient 148 has begun transit to the healthcare facility for the healthcare appointment. The first message may comprise a (current) location of the patient 148 (e.g., a set of global positioning system (GPS) coordinates) and patient information for the patient 148. In an embodiment, the patient computing device 146 may ascertain the location of the patient 148 by way of the geolocation receiver 216. In another embodiment, the patient computing device 146 may receive input from the patient 148 indicative of the location of the patient 148 (e.g., an address). The patient computing device 146 may transmit the location to an Internet-based mapping service which may determine the location of the patient 148 based on the address. The Internet-based mapping system may then transmit the location of the patient 148 to the patient computing device 146, which may forward the location to the server EHR 108. The patient computing device 146 may also transmit the address to the server EHR 108 which may communicate with the Internet-based mapping service in order to determine the location of the patient 148.

The patient information for the patient 148 may include an identifier for the patient 148 (e.g., a name, a medical record number (MRN), etc.), an age of the patient 148, an address of the patient 148, insurance information of the patient 148, a list of allergies of the patient 148, and/or a list of (active) medications of the patient 148.

In an embodiment, the patient computing device 146 may receive the patient information as manual input from the patient 148. The patient computing device 146 may store the patient information in the data store 206 of the patient computing device 146 for future use. Thus, for future healthcare appointment, the patient computing device 146 need not receive the patient information as manual input from the patient 148.

In another embodiment, the first message includes an identifier for the patient 148, but fails to include at least a portion of the patient information for the patient 148. As such, the patient computing device 146 may receive input from the patient 148 causing the client patient portal application 204 to transmit the identifier for the patient 148 to the server patient portal application. Responsive to receiving the identifier for the patient 148, the server patient portal application may execute a search over a data store retaining patient information for a plurality of patients. The search is based on the identifier for the patient 148. The search produces search results, wherein the search results include the at least a portion of the patient information for the patient 148. The server patient portal application then causes the at least a portion of the patient information for the patient 148 to be included in the first message. The server patient portal application then routes the first message to the server EHR 108.

The server EHR 108 may then receive the first message. Responsive to receiving the first message, the server EHR 108 may cause the patient information for the patient 148 to be stored in the cache 112. In an embodiment, the patient information for the patient 148 may be stored in denormalized form so as to facilitate fast read read-times for the patient information. In an embodiment, the server EHR 108 may utilize stored procedures in order to facilitate storing the patient information in tables stored in the cache 112.

It is understood that the clinical data for the patient 148 retained in the data store 114 of the server computing device 102 may not represent the complete patient record for the patient 148. For instance, the clinical data for the patient 148 retained in the data store 114 may not include all of the active medications of the patient 148 and/or all of the allergies of the patient 148. Thus, in an embodiment, subsequent to receiving the first message, the server EHR 108 may transmit an identifier for the patient 148 to the EHR agent executing on the second server computing device 142. The EHR agent may then retrieve additional patient information (e.g., active medications of the patient 148, allergies of the patient 148, etc.) for the patient 148. For instance, the EHR agent may execute a search over a data store (not shown) accessible to the EHR agent that comprises clinical data for patients gathered from different sources (e.g., different EHR systems, HIEs, third-party applications, etc.) that are inaccessible to the server EHR 108. The search may be based upon the identifier for the patient 148. The search produces search results, wherein the search results include the additional patient information for the patient 148. The EHR agent may then transmit the additional patient information to the server EHR 108 which may cause the additional information for the patient 148 to become part of the patient information for the patient 148. The server EHR 108 may then store the patient information in the cache 112 as described above. Alternatively, the server patient portal application may perform the aforementioned steps in place of the server EHR 108 in order to retrieve the additional patient information for the patient 148.

Additionally, the server EHR 108 also places a placeholder for the patient 148 in a computer-implemented queue for healthcare appointments at the healthcare facility. The queue comprises placeholders for healthcare appointments at the healthcare facility. An ordering of the placeholders in the queue is indicative of an order in which the healthcare appointments are scheduled to occur at the healthcare facility. A position of the placeholder in the queue is based upon the datetime for the healthcare appointment and a distance between the location of the patient 148 and a location of the healthcare facility.

The server EHR 108 may be configured to dynamically rearrange the queue for the healthcare appointments if the patient 148 (or another patient) will fail to arrive at the healthcare facility for the datetime of the healthcare appointment (or another healthcare appointment). In an example, the queue comprises a second placeholder for a second patient that has a second healthcare appointment at the healthcare facility at a second datetime. The second datetime may occur immediately after the datetime and as such the second placeholder is placed immediately after the placeholder within the queue. In the example, the server EHR 108 receives a current location of the patient 148 from the patient computing device 146 at predefined intervals (e.g., every minute). The server EHR 108 may also receive a current location of the second patient from a second patient computing device operated by the second patient. The server EHR 108 may determine that the patient 148 will fail to arrive at the healthcare facility at the datetime based on the current location of the patient 148 and a current datetime. The determination may also be made based upon traffic data for areas surrounding the current location of the patient 148 and/or the healthcare facility received from an Internet-based mapping service. The server EHR 108 may also determine that the second patient will arrive at the healthcare facility prior to or at the datetime based on the current location of the second patient. The determination may also be made upon traffic data for areas surrounding the current location of the patient 148 received from the Internet-based mapping service. Responsive to determining that the patient 148 will fail to arrive at the healthcare facility at the datetime for the healthcare appointment, the server EHR 108 may reposition the placeholder for the patient 148 in the queue such that the placeholder is placed immediately after the second placeholder in the queue, thereby indicating that the healthcare appointment datetimes have been switched. The server EHR 108 may also cause a notification to be transmitted to the patient computing device 146 (e.g., by way of the server patient portal application) indicating that the healthcare appointment for the patient 148 has been rescheduled to a different datetime due to the determination that the patient 148 will fail to arrive at the healthcare facility at the datetime.

In another example, the second healthcare appointment for the second patient is scheduled for a second datetime at the healthcare facility that occurs immediately before the datetime of the healthcare appointment. As such, the second placeholder for the second patient in the queue is placed immediately before the placeholder for the first patient in the queue. In the example, the server EHR 108 may determine that the second patient will fail to arrive at the healthcare facility at the second datetime. The server EHR 108 may also receive a current location of the patient 148. The server EHR 108 may determine that the patient 148 will arrive at the healthcare facility prior to or at the second datetime based in part upon the second location (as well as potentially traffic data received from an Internet-based mapping service). Responsive to determining that the second patient will fail to arrive at the healthcare facility, the server EHR 108 repositions the placeholder for the patient 148 within the queue such that the placeholder is placed immediately before the second placeholder in the queue.

The server EHR 108 may also cause a notification to be received by the patient computing device 146 (e.g., by way of the server patient portal application). The notification may indicate that the second datetime is now available for the healthcare appointment of the patient 148 due to a cancellation (or reschedule). The notification may include the option to allow the patient 148 to reschedule the healthcare appointment for the second datetime. If the patient 148 wishes to take the (earlier) second datetime, the patient computing device 146 may receive input from the patient indicating that the patient 148 agrees to the second datetime for the healthcare appointment, and the patient computing device 146 may transmit data causing the server EHR 108 to schedule the healthcare appointment for the (now free) second datetime.

In an embodiment, the server EHR 108 may be configured to transmit data that causes a visual representation of the queue to be presented on the display 210 of the patient computing device 146 and/or the display 134 of the client computing device 122 (described below).

When the patient 148 arrives at the healthcare facility, the patient computing device 146 may cause a second message to be received by the server EHR 108. The second message indicates that the patient 148 has arrived at (or is about to arrive at) the healthcare facility for the healthcare appointment. The second message may include the identifier for the patient. In an embodiment, the patient computing device 146 may determine a current location of the patient 148 by way of the geolocation receiver 216. The patient computing device 146 may also determine a location of the healthcare facility. When the current location of the patient 148 is within a certain threshold distance of the location of the healthcare facility, the patient computing device 146 can cause the second message to be generated. In another embodiment, when the patient 148 arrives at the healthcare facility, the patient computing device 146 may receive input from the patient 148 causing the patient computing device 146 to generate the second message.

In an embodiment, the client patient portal application 204 executing on the patient computing device 146 may transmit the second message to the server patient portal application. The server patient portal application may then transmit the second message to the server EHR 108. In another embodiment, the patient computing device 146 may directly transmit the second message to the server EHR 108.

Responsive to receiving the second message, the server EHR 108 may transfer the patient information for the patient 148 from the cache 112 to the data store 114. The server EHR 108 may cause the patient information for the patient 148 from the cache 112 to be stored as part of the clinical data for the patient 148. In an embodiment, the patient information may be stored in a normalized form (e.g., 3NF, 4NF, etc.) in the data store 114. The server EHR 108 may also transmit the patient information for the patient 148 to the client EHR 128, whereupon the client EHR 128 may present the patient information for the patient 148 on the display 134. In an embodiment, the electronic prescription module 110 may then utilize the patient information for the patient 148 in the data store 114 to generate an electronic prescription for the patient 148. Subsequently, the server EHR 108 may purge the patient information from the cache 112. The server EHR 108 may also remove the placeholder for the patient 148 from the queue after the healthcare appointment for the patient 148 has concluded.

Although the above-described processes have been primarily described as being performed by the server EHR 108, other possibilities are contemplated. For instance, some or all of the above-described processes may be performed by a standalone application executing on a different server computing device than the server computing device 102.

Figure 3:
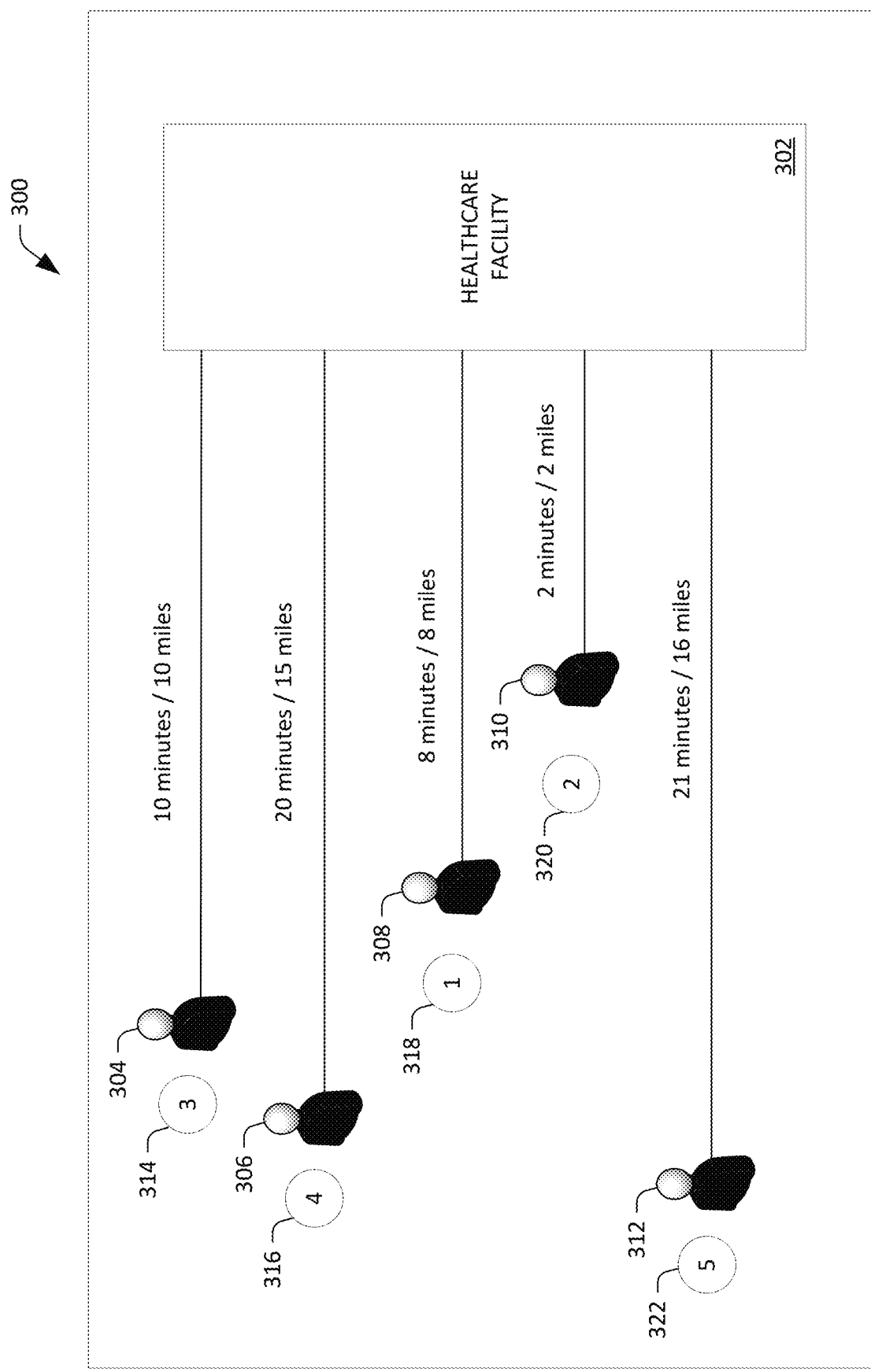
FIG. 3 is an illustration of an exemplary graphical user interface (GUI) that can be presented on a display of a computing device.

Turning now to FIG. 3, an exemplary GUI 300 that can be presented on a display of a computing device is depicted. In an example, the GUI 300 may be presented on the display 210 of the patient computing device 146 as part of the graphical features 212. In another example, the GUI 300 may be presented on the display 134 of the client computing device 122 as part of the graphical features 136. The GUI 300 comprises a visual indicator for a healthcare facility 302 at which healthcare appointments are to occur, as well as visual indicators of patients 304-312 that are to attend their respective healthcare appointments. The visual indicators of the patients 304-312 may be arranged such that patients that are closer to the healthcare facility are depicted as closer to the visual indicator for the healthcare facility 302 and patients that are farther away from the healthcare facility are depicted as farther away from the visual indicator for the healthcare facility 302. For instance, in the GUI 300, the visual indicator 310 is closer to the visual indication of the healthcare facility 302 than the visual indicator 312 is from the visual indication of the healthcare facility 302.

The GUI 300 additionally includes ordering markings 314-322. Each ordering marking in the ordering markings 314-322 is indicative of an order in which the healthcare appointments are scheduled to occur. Thus, the GUI 300 may serve as a visual representation of a queue for healthcare appointments at the healthcare facility. In the example shown in the GUI 300, a first patient is represented by the visual indicator 308 and a second patient is indicated by the visual indicator 310. The first patient is to attend a first healthcare appointment at the healthcare facility and the second patient is to attend a second healthcare appointment at the healthcare facility. The first healthcare appointment is scheduled to occur prior to the second healthcare appointment. However, the GUI 300 indicates that the first patient is 8 miles away from the healthcare facility and the second patient is 2 miles away from the healthcare facility. In an example, the EHR may determine that the first patient will fail to arrive at the healthcare facility for the first datetime. Therefore, as described above, the EHR may utilize the above-described processes to reschedule the first healthcare appointment. For instance, the EHR may swap datetimes for the first healthcare appointment and the second healthcare appointment.

With reference now to FIG. 4, a depiction 400 of tables 402-408 that may be stored in the cache 112 is illustrated. The tables 402-408 may include a table for insurers 402 of patients, a table for allergies 404 of patients, a table for medications 406 of patients, and a table for demographic information 408 of patients. As described above, when the patient 148 arrives at the healthcare facility, the server EHR 108 (or the electronic prescription module 110 of the server EHR 108) may cause data in the tables 402-408 to be transferred from the cache 112 to the data store 114. While the tables 402-408 are depicted as four separate tables, in an embodiment, it is to be understood that information retained in the tables 402-408 may be retained in a single table.

Figure 5:
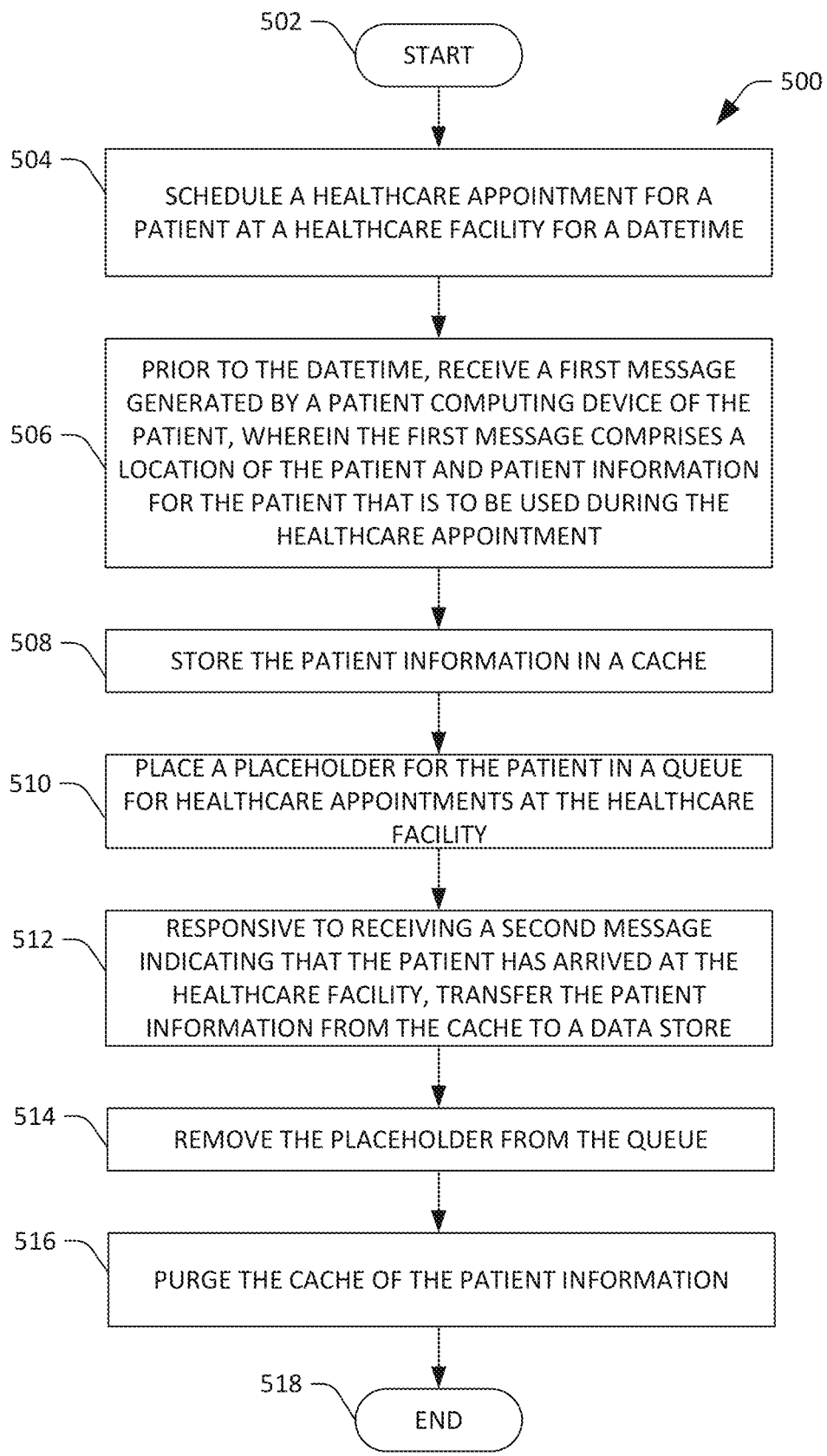
FIG. 5 is a flow diagram that illustrates an exemplary methodology executed by an electronic health records application for patient check-in for healthcare appointments.
Figure 6:
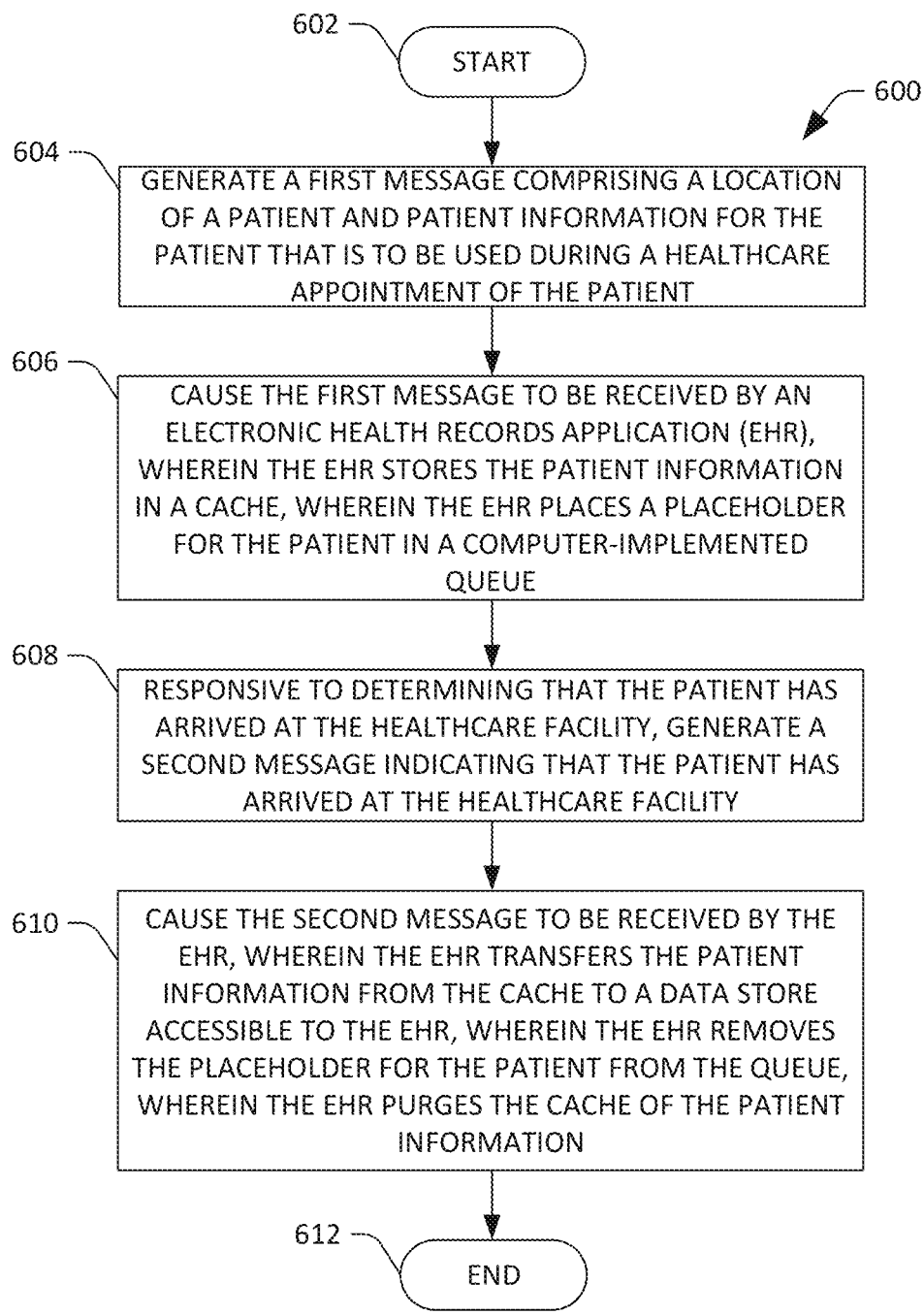
FIG. 6 is a flow diagram that illustrates an exemplary methodology executed by a patient computing device for patient check-in for healthcare appointments.

FIGS. 5 and 6 illustrate exemplary methodologies relating to patient-check-in for a healthcare appointment. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 5, a methodology 500 executed by an EHR that facilitates patient check-in for a healthcare appointment is illustrated. The methodology 500 begins at 502, and at 504 the EHR schedules a healthcare appointment for a patient at a healthcare facility for a datetime. At 506, prior to the datetime, the EHR receives a first message originating from a patient computing device of the patient. The first message comprises a location of the patient and patient information for the patient that is to be used during the healthcare appointment. At 508, responsive to receiving the first message, the EHR stores the patient information in a cache accessible to the EHR. At 510, the EHR places a placeholder for the patient in a computer-implemented queue comprising placeholders for healthcare appointments at the healthcare facility. An ordering of the placeholders in the queue is indicative of an order in which the healthcare appointments are to occur at the healthcare facility and a position of the placeholder in the queue is based upon the datetime for the healthcare appointment and a distance between the location of the patient and a location of the healthcare facility.

At 512, responsive to receiving a second message indicating that the patient has arrived at the healthcare facility, the EHR transfers the patient information from the cache into a data store accessible to the EHR such that the patient information is stored in the data store. At 514, the EHR removes the placeholder for the patient from the queue. At 516, the EHR purges the cache of the patient information. The methodology 500 concludes at 518.

Turning now to FIG. 6, a methodology 600 executed by a patient computing device that facilitates patient check-in for a healthcare appointment is illustrated. The methodology 600 begins at 602, and at 604 the patient computing device generates a first message. The first message comprises a location of the patient and patient information for the patient that is to be used during a healthcare appointment of the patient. At 606, the patient computing device causes the first message to be received by an EHR. The EHR stores the patient information in a cache. The EHR also places a placeholder for the patient in a computer-implemented queue comprising placeholders for healthcare appointments at the healthcare facility. An ordering of the placeholders in the queue is indicative of an order in which the healthcare appointments are to occur at the healthcare facility and a position of the placeholder in the queue is based upon the datetime for the healthcare appointment and a distance between the location of the patient and a location of the healthcare facility. At 608, responsive to determining that the patient has arrived at the healthcare facility, the patient computing device generates a second message indicating that the patient has arrived at the healthcare facility for the healthcare appointment. Alternatively, the patient computing device may generate the second message at a certain time or in response to determining that the patient has traveled a certain threshold distance to the healthcare facility. At 610, the patient computing device causes the second message to be received by the EHR. The EHR then transfers the patient information for the patient from the cache to a data store accessible to the EHR. The EHR then removes the placeholder for the patient from the queue and purges the cache of the patient information. The methodology 600 concludes at 612.

Figure 7:
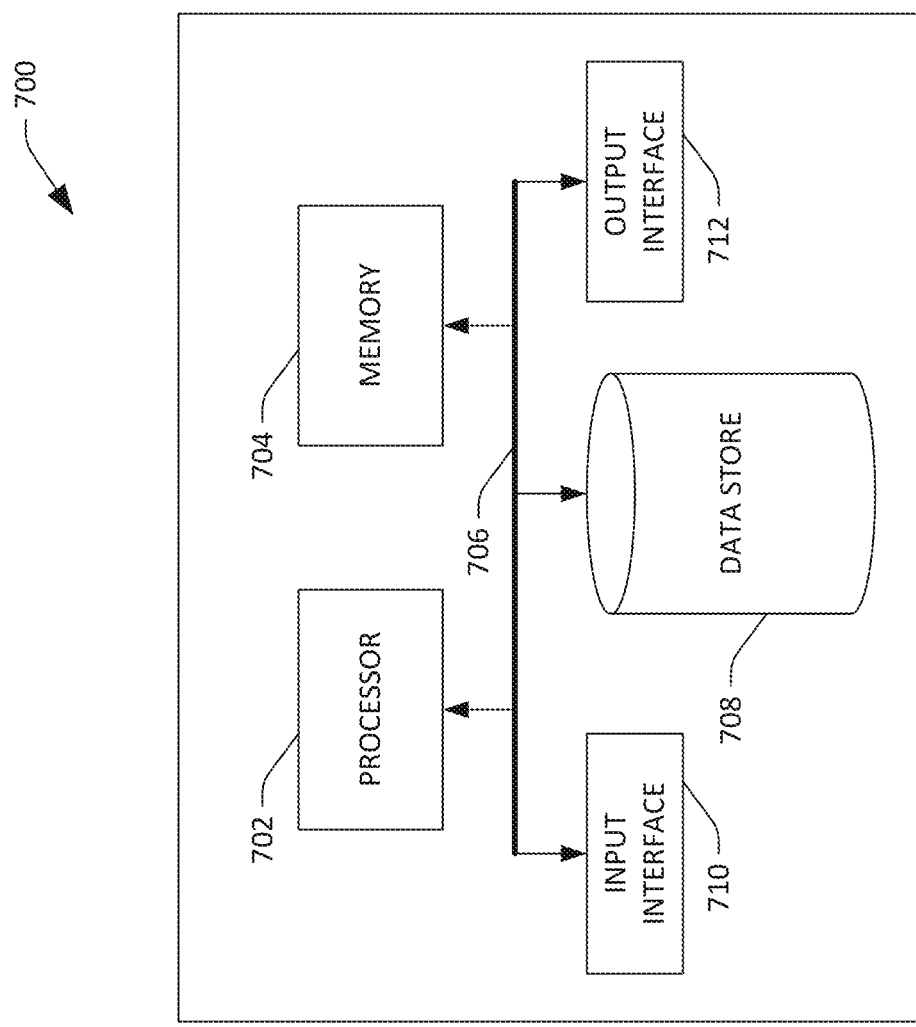
FIG. 7 is an exemplary computing system.

Referring now to FIG. 7, a high-level illustration of an exemplary computing device 700 that can be used in accordance with the systems and methodologies disclosed herein is illustrated. For instance, the computing device 700 may be used in a system that dynamically rearranges a computer-implemented queue for healthcare appointments for patients based in part on patient proximity to a healthcare facility in which the healthcare appointments are to occur. By way of another example, the computing device 700 can be used in a system that displays a visual representation of the computer-implemented queue on a display. The computing device 700 includes at least one processor 702 that executes instructions that are stored in a memory 704. The instructions may be, for instance, instructions for implementing functionality described as being carried out by one or more components discussed above or instructions for implementing one or more of the methods described above. The processor 702 may access the memory 704 by way of a system bus 706. In addition to storing executable instructions, the memory 704 may also store clinical data, appointment data, computer-implemented queues, etc.

The computing device 700 additionally includes a data store 708 that is accessible by the processor 702 by way of the system bus 706. The data store 708 may include executable instructions, clinical data, appointment data, computer-implemented queues, etc. The computing device 700 also includes an input interface 710 that allows external devices to communicate with the computing device 700. For instance, the input interface 710 may be used to receive instructions from an external computer device, from a user, etc. The computing device 700 also includes an output interface 712 that interfaces the computing device 700 with one or more external devices. For example, the computing device 700 may display text, images, etc. by way of the output interface 712.

It is contemplated that the external devices that communicate with the computing device 700 via the input interface 710 and the output interface 712 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 700 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 700 may be a distributed system. Thus, for instance, several devices may be in communication by way of a network connection and may collectively perform tasks described as being performed by the computing device 700.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device comprising:
a processor; and
memory storing a server electronic health records application (server EHR) that, when executed by the processor, causes the processor to perform acts comprising:
scheduling a healthcare appointment for a patient at a healthcare facility for a datetime;
prior to the datetime, receiving, over a network connection, a first message originating from a patient computing device of the patient, wherein the first message comprises:
a location of the patient; and
patient information for the patient that is to be used during the healthcare appointment;
responsive to receiving the first message and without storing the patient information in a computer-readable data store accessible to the server EHR, storing the patient information in a computer-readable cache accessible to the server EHR;
placing a placeholder for the patient in a computer-implemented queue comprising placeholders for healthcare appointments for patients at the healthcare facility, wherein an ordering of the placeholders in the queue is indicative of an order in which the healthcare appointments are to occur at the healthcare facility, wherein a position of the placeholder in the queue is based upon the datetime for the healthcare appointment and a distance between the location of the patient and a location of the healthcare facility;

causing data to be transmitted to the patient computing device over the network connection, wherein the data causes the patient computing device to present a visual representation of the queue on a display of the patient computing device, wherein the visual representation of the queue comprises:

first visual icons assigned to the patients that have the healthcare appointments at the healthcare facility;

second visual icons assigned to the first visual icons, wherein the second visual icons are indicative of the order in which the healthcare appointments are to occur; and third visual icons assigned to the first visual icons, wherein the third visual icons are indicative of distances of each of the patients to the healthcare facility; and responsive to receiving, over the network connection, a second message indicating that the patient has arrived at the healthcare facility, transferring the patient information from the computer-readable cache into the computer-readable data store accessible to the server EHR.

2. The server computing device of claim 1, the acts further comprising:

transmitting, over a second network connection, the patient information to a client electronic health records application (client EHR) executing on a client computing device, wherein the patient information is presented by the client EHR to a healthcare worker on a display of the client computing device.

3. The server computing device of claim 1, wherein the patient information for the patient includes an identifier for the patient, the acts further comprising:

subsequent to receiving the first message and prior to transferring the patient information from the computer-readable cache into the computer-readable data store, transmitting, over a second network connection, the identifier for the patient to an electronic health records agent application (EHR agent) executing on a second server computing device, wherein a list of active medications of the patient and a list of allergies for the patient are retrieved by the EHR agent from sources inaccessible to the server EHR, wherein the list of active medications and the list of allergies are transmitted by the EHR agent to the server EHR; and responsive to receiving the list of active medications and the list of allergies, storing the list of active medications and the list of allergies in the computer-readable cache as part of the patient information.

4. The server computing device of claim 1, wherein a second healthcare appointment for a second patient is scheduled for a second datetime at the healthcare facility, wherein the second datetime occurs immediately after the datetime, wherein the queue further comprises a second placeholder for the second patient that is placed immediately after the placeholder for the patient in the queue, the acts further comprising:

subsequent to receiving the first message and prior to receiving the second message, receiving, over the network connection, a second location of the patient generated by the patient computing device;

receiving, over a second network connection, a third location of the second patient generated by a second patient computing device operated by the second patient;

determining that the second patient will arrive at the healthcare facility prior to or at the datetime based in part upon the third location; and responsive to determining that the patient will fail to arrive at the healthcare facility at the datetime based in part upon the second location of the patient, repositioning the placeholder for the patient in the queue such that the placeholder is placed immediately after the second placeholder in the queue.

5. The server computing device of claim 4, wherein determining that the patient will fail to arrive at the healthcare facility at the datetime is further based upon first traffic data received from an Internet-based mapping service, wherein determining that that the second patient will arrive at the healthcare facility prior to or at the datetime is further based upon second traffic data received from the Internet-based mapping service.

6. The server computing device of claim 4, the acts further comprising:

causing a third message to be transmitted to the patient computing device over the network connection, wherein the third message includes the second datetime for the healthcare appointment, wherein the second datetime is presented on a display of the patient computing device.

7. The server computing device of claim 1, wherein the patient computing device comprises a geolocation receiver, wherein the location of the patient is determined using the geolocation receiver.

8. The server computing device of claim 1, wherein the patient information comprises:

an identifier for the patient;
a sex of the patient;
an age of the patient;
an address of the patient;
insurance information of the patient;
a list of allergies of the patient; and
a list of medications of the patient.

9. The server computing device of claim 1, wherein the first message includes an identifier for the patient, wherein the first message initially fails to include at least a portion of the patient information for the patient, wherein a client patient portal application is executed by the patient computing device, wherein the first message is transmitted, over a second network connection, by the client patient portal application to a server patient portal application executing on a second server computing device, wherein the at least a portion of the patient information is retrieved by the server patient portal application from a second computer-readable data store based upon the identifier for the patient, wherein the at least a portion of the patient information is caused by the server patient portal application to be included in the first message, wherein the first message is routed by the server patient portal application to the server EHR.

10. The server computing device of claim 1, the acts further comprising:

subsequent to transferring the patient information from the computer-readable cache into the computer-readable data store, removing the placeholder for the patient from the queue; and purging the computer-readable cache of the patient information.

11. A method performed by a server electronic health records application (server EHR) executing on a server computing device, the method comprising:
- scheduling a healthcare appointment for a patient at a healthcare facility for a datetime;
- prior to the datetime, receiving, over a network connection, a first message originating from a patient computing device of the patient, wherein the first message comprises:
  - a location of the patient; and
  - patient information for the patient that is to be used during the healthcare appointment;
- responsive to receiving the first message and without storing the patient information in a computer-readable data store accessible to the server EHR, storing the patient information in a computer-readable cache accessible to the server EHR;
- placing a placeholder for the patient in a computer-implemented queue comprising placeholders for healthcare appointments for patients at the healthcare facility, wherein an ordering of the placeholders in the queue is indicative of an order in which the healthcare appointments are to occur at the healthcare facility, wherein a position of the placeholder in the queue is based upon the datetime for the healthcare appointment and a distance between the location of the patient and a location of the healthcare facility;
- causing data to be transmitted to the patient computing device over the network connection, wherein the data causes the patient computing device to present a visual representation of the queue on a display of the patient computing device, wherein the visual representation of the queue comprises:
  - first visual icons assigned to the patients that have the healthcare appointments at the healthcare facility;
  - second visual icons assigned to the first visual icons, wherein the second visual icons are indicative of the order in which the healthcare appointments are to occur; and
  - third visual icons assigned to the first visual icons, wherein the third visual icons are indicative of distances of each of the patients to the healthcare facility;
- responsive to receiving, over the network connection, a second message indicating that the patient has arrived at the healthcare facility, transferring the patient information from the computer-readable cache into the computer-readable data store accessible to the server EHR such that the patient information is stored in the computer-readable data store;
- removing the placeholder for the patient from the queue; and
- purging the computer-readable cache of the patient information.

12. The method of claim 11, wherein the patient information for the patient includes an identifier for the patient, the method further comprising:
- subsequent to receiving the first message and prior to transferring the patient information from the computer-readable cache into the computer-readable data store, transmitting, over a second network connection, the identifier for the patient to an electronic health records agent application (EHR agent), wherein a list of active medications of the patient and a list of allergies for the patient are retrieved by the EHR agent from sources inaccessible to the server EHR, wherein the list of active medications and the list of allergies are transmitted by the EHR agent to the server EHR; and
- responsive to receiving the list of active medications and the list of allergies, storing the list of active medications and the list of allergies in the computer-readable cache as part of the patient information.

13. The method of claim 11, wherein the first message includes an identifier for the patient, wherein the first message initially fails to include at least a portion of the patient information for the patient, wherein a client patient portal application is executed by the patient computing device, wherein the first message is transmitted, over a second network connection, by the client patient portal application to a server patient portal application executing on a second server computing device, wherein the at least a portion of the patient information is retrieved by the server patient portal application from a second computer-readable data store based upon the identifier for the patient, wherein the at least a portion of the patient information is caused by the server patient portal application to be included in the first message, wherein the first message is routed by the server patient portal application to the server EHR.

14. The method of claim 11, wherein the patient information stored in the computer-readable cache is stored in a denormalized form, wherein the patient information stored in the computer-readable data store is stored in one of:
- third normal form (3NF);
- elementary key normal form (EKNF);
- Boyce-Codd normal form (BCNF);
- fourth normal form (4NF);
- essential tuple normal form (ETNF);
- fifth normal form (5NF);
- domain-key normal form (DKNF); or
- sixth normal form (6NF).

15. The method of claim 11, the method further comprising:
- transmitting, over a second network connection, second data to a client electronic health records application (client EHR) executing on a client computing device, wherein the second data causes the client EHR to present the visual representation of the queue on a display of the client computing device.

16. The method of claim 11, wherein a second healthcare appointment for a second patient is scheduled for a second datetime at the healthcare facility, wherein the second datetime occurs immediately before the datetime, wherein the queue further comprises a second placeholder for the second patient that is placed immediately before the placeholder for the patient in the queue, the method further comprising:
- receiving, over the network connection, a second location of the patient generated by the patient computing device;
- determining that the patient will arrive at the healthcare facility prior to or at the second datetime based in part upon the second location; and
- responsive to determining that the second patient will fail to arrive at the healthcare facility at the second datetime, repositioning the placeholder for the patient in the queue such that the placeholder is placed immediately before the second placeholder in the queue.

17. The method of claim 11, wherein the patient information for the patient is received by the patient computing device as input from the patient.

18. The method of claim 11, wherein the patient information comprises:
- an identifier for the patient;
- a sex of the patient;

an age of the patient;
an address of the patient;
insurance information of the patient;
a list of allergies of the patient; and
a list of medications of the patient.

19. A non-transitory computer-readable storage medium comprising an electronic prescription module of a server electronic health records application (server EHR) that, when executed by a processor of a server computing device, causes the processor to perform acts comprising:
  scheduling a healthcare appointment for a patient at a healthcare facility for a datetime, wherein a medication is to be prescribed to the patient during the healthcare appointment;
  prior to the datetime, receiving, over a network connection, a first message originating from a patient computing device of the patient, wherein the first message comprises:
    a location of the patient; and
    patient information for the patient that is to be used during the healthcare appointment;
  responsive to receiving the first message and without storing the patient information in a computer-readable data store accessible to the server EHR, storing the patient information in a computer-readable cache accessible to the server EHR;
  placing a placeholder for the patient in a computer-implemented queue comprising placeholders for healthcare appointments for patients at the healthcare facility, wherein an ordering of the placeholders in the queue is indicative of an order in which the healthcare appointments are to occur at the healthcare facility, wherein a position of the placeholder in the queue is based upon the datetime for the healthcare appointment and a distance between the location of the patient and a location of the healthcare facility;
  causing data to be transmitted to the patient computing device over the network connection, wherein the data causes the patient computing device to present a visual representation of the queue on a display of the patient computing device, wherein the visual representation of the queue comprises:
    first visual icons assigned to the patients that have the healthcare appointments at the healthcare facility;
    second visual icons assigned to the first visual icons, wherein the second visual icons are indicative of the order in which the healthcare appointments are to occur; and
    third visual icons assigned to the first visual icons, wherein the third visual icons are indicative of distances of each of the patients to the healthcare facility; and
  responsive to receiving, over the network connection, a second message indicating that the patient has arrived at the healthcare facility, transferring the patient information from the computer-readable cache into the computer-readable data store accessible to the electronic prescription module, wherein the electronic prescription module utilizes the patient information in generating the electronic prescription for the patient.

20. The non-transitory computer-readable storage medium of claim 19, wherein the patient information comprises:
  an identifier for the patient;
  a sex of the patient;
  an age of the patient;
  an address of the patient;
  insurance information of the patient;
  a list of allergies of the patient; and
  a list of medications of the patient.

\* \* \* \* \*